US00PP16166P2

(12) United States Plant Patent

Van Huylenbroeck

(10) Patent No.: US PP16,166 P2
(45) Date of Patent: Dec. 20, 2005

(54) *HYDRANGEA* PLANT NAMED 'DVP PINKY'

(50) Latin Name: *Hydrangea paniculata*
Varietal Denomination: DVP Pinky

(75) Inventor: Johan Van Huylenbroeck, Melle (BE)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 10/968,806

(22) Filed: Oct. 19, 2004

(51) Int. Cl.[7] ..... A01H 5/00
(52) U.S. Cl. ..... Plt./250
(58) Field of Search ..... Plt./250

(56) References Cited

PUBLICATIONS

UPOV–ROM GTITM Plant Variety Database, 2005/01, GTI Jouve Retrieval Software, Citation for *Hydrangea* 'Dvp-pinky'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Hydrangea* plant named 'DVP Pinky', characterized by its upright and somewhat outwardly spreading plant habit; large upright flower panicles; and large panicles with white-colored sterile flowers that become purple in color during the fall.

1 Drawing Sheet

Botanical classification/cultivar designation: *Hydrangea paniculata* cultivar DVP Pinky.

BACKGROUND OF THE INVENTION

The present Invention relates to a new and distinct cultivar of *Hydrangea* plant, botanically known as *Hydrangea paniculata,* and hereinafter referred to by the cultivar name DVP Pinky.

The new *Hydrangea* originated from an open-pollination in 1997 of the *Hydrangea paniculata* cultivar Pink Diamond, not patented, as the female, or seed, parent with an unknown selection of *Hydrangea paniculata,* not patented, as the male, or pollen, parent. The cultivar DVP Pinky was discovered and selected by the Inventor as a single plant within the progeny of the stated open-pollination in a controlled environment in Melle, Belgium in 1999.

Asexual reproduction of the new cultivar by softwood cuttings taken in Melle, Belgium since the summer of 2002, has shown that the unique features of this new *Hydrangea* are stable and reproduced true to type in successive generations.

SUMMARY OF THE INVENTION

Plants of the cultivar DVP Pinky have not been observed under all possible environmental conditions. The phenotype may vary somewhat with variations in environment such as temperature and light intensity without, however, any variance in genotype.

The following traits have been repeatedly observed and are determined to be the unique characteristics of 'DVP Pinky'. These characteristics in combination distinguish 'DVP Pinky' as a new and distinct cultivar:

1. Upright and somewhat outwardly spreading plant habit.
2. Large upright flower panicles.
3. Large panicles with white-colored sterile flowers that become purple in color during the fall.

Plants of the new *Hydrangea* are most similar to plants of the female parent, the cultivar Pink Diamond. In side-by-side comparisons conducted in Grand Haven, Mich., plants of the new *Hydrangea* differed from plants of the cultivar Pink Diamond in the following characteristics:

1. Plants of the new *Hydrangea* were not as outwardly spreading as plants of the cultivar Pink Diamond.
2. Plants of the new *Hydrangea* were more freely branching than plants of the cultivar Pink Diamond.
3. Plants of the new *Hydrangea* had more sterile flowers per inflorescence than plants of the cultivar Pink Diamond.
4. Plants of the new *Hydrangea* had larger sterile flowers than plants of the cultivar Pink Diamond.
5. Plants of the new *Hydrangea* and the cultivar Pink Diamond differed in flower coloration in the fall as flowers of plants of the new *Hydrangea* were darker in color than flowers of the cultivar Pink Diamond.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph at the bottom of the first sheet is a side perspective view of a typical plant of 'DVP Pinky' in August showing the purple coloration that develops during the late summer.

The photograph at the top of the sheet comprises a close-up view of a typical inflorescence of 'DVP Pinky' in July prior to the flower color change.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. During the production of the plants, day temperatures ranged from 20 to 30° C., and night temperatures ranged from 12 to 20° C. Plants were about two years old when the photographs and description were taken. Photographs and description were taken during the summer and fall.

Botanical classification: *Hydrangea paniculata* cultivar DVP Pinky.

Parentage:

*Female, or seed, parent.*—*Hydrangea paniculata* cultivar Pink Diamond, not patented.

*Male, or pollen, parent.*—Unknown *Hydrangea paniculata* selection, not patented.

Propagation:

*Type cutting.*—By softwood cuttings.

*Time to initiate roots.*—About 20 days at 20° C.

*Time to produce a rooted cutting or liner.*—About two months at 20° C.

*Root description.*—Thick; creamy white in color.

*Rooting habit.*—Freely branching; dense.

Plant description:

*Form/growth habit.*—Upright and somewhat outwardly spreading plant habit; inverted triangle; dense and bushy perennial shrub. Vigorous growth habit.

*Plant height, soil level to top of plant plane.*—About 1 meter.

*Plant diameter or area of spread.*—About 75 cm.

*Branching habit.*—Freely branching, about 15 lateral branches per plant. Pruning will enhance branching potential.

*Lateral branches.*—Length: About 1 meter. Diameter: About 6 mm. Internode length: About 3.4 cm. Strength: Very strong. Texture: Smooth, glabrous. Color: 187B.

*Foliage description.*—Arrangement: Opposite, simple. Length: About 14.5 cm. Width: About 5.5 cm. Shape: Elliptic to ovate. Apex: Acute to acuminate. Base: Cuneate. Margin: Serrate. Texture, upper and lower surfaces: Slightly, pubescent; rugose. Venation pattern: Pinnate. Color: Developing and fully expanded foliage, upper surface: 147A. Developing and fully expanded foliage, lower surface: 138A. Venation, upper surface: 144C. Venation, lower surface: 144B. Petiole: Length: About 3.1 cm. Diameter: About 2 mm. Texture, upper and lower surfaces: Smooth, glabrous. Color, upper and lower surfaces: 187B.

Flower description:

*Flower type and habit.*—Single fertile and sterile flowers arranged on large terminal panicles. Sterile flowers with large showy sepals, but without petals and reproductive organs. Fertile flowers, inconspicuous, but with petals, sepals and reproductive organs. Sterile flowers persistent; fertile flowers not persistent. Fertile and sterile flowers are not fragrant.

*Natural flowering season.*—Continuously flowering from summer through fall in Grand Haven, Mich.

*Flower longevity.*—Sterile flowers last about 18 weeks on the plant. As cut flowering stems, panicles last about four weeks.

*Quantity of flowers.*—Freely flowering; one terminal panicle per lateral branch with about 325 sterile flowers and about 242 fertile flowers per panicle.

*Panicle height.*—About 28 cm.

*Panicle diameter.*—About 17 cm.

*Panicle shape.*—Conical.

*Flower diameter.*—Sterile flowers: About 6 cm. Fertile flowers: About 9 mm.

*Flower depth (height).*—Sterile flowers: About 1.5 cm. Fertile flowers: About 8 mm.

*Flower buds, fertile and sterile flowers.*—Length: About 4 mm. Diameter: About 3 mm. Shape: Elliptic. Color: 141D.

*Petals (petals present only on fertile flowers; sterile flowers do not have petals).*—Arrangement: About five. Length: About 3 mm. Width: About 2 mm. Shape: Lanceolate. Apex: Acute. Base: Truncate. Margin: Entire. Texture, upper and lower surfaces: Smooth, glabrous. Color: When opening, upper and lower surfaces: 155D. Fully opened, upper and lower surfaces: 155D.

*Sepals.*—Quantity per flower: Fertile flowers: About five, fused into a calyx. Sterile flowers: About seven. Length: Fertile flowers: Less than 1 mm. Sterile flowers: About 3.1 cm. Width: Fertile flowers: Less than 1 mm. Sterile flowers: About 1.9 cm. Shape: Fertile flowers: Connate. Sterile flowers: Obovate. Apex: Fertile flowers: Acute. Sterile flowers: Obtuse to retuse. Base: Fertile flowers: Fused. Sterile flowers: Cuneate. Margin, fertile and sterile flowers: Entire. Texture, fertile and sterile flowers, upper and lower surfaces: Smooth, glabrous. Color: Fertile flowers: When opening and fully opened, upper and lower surfaces, 155A. Sterile flowers: When opening, upper and lower surfaces: 145B. Fully opened, upper and lower surfaces: 155D; color transitioning through various shades of pink to eventually to 186A with development towards the end of summer.

*Peduncles.*—Angle: Mostly erect. Strength: Strong. Length: About 27 cm. Diameter: About 4 mm. Texture: Smooth. Color flowers: 147D.

*Pedicels.*—Angle, fertile and sterile flowers: Variable, dependent on position in the panicle; erect to about 90° from vertical. Strength, fertile and sterile flowers: Strong. Length: Fertile flowers: About 2 mm. Sterile flowers: About 2.3 cm. Diameter: Fertile flowers: About 1 mm. Sterile flowers: About 1.5 mm. Texture, fertile and sterile flowers: Smooth. Color, fertile and sterile flowers: 155A.

*Reproductive organs (reproductive organs present only on fertile flowers; sterile flowers do not have reproductive organs).*—Stamens: Quantity per flower: About ten. Anther shape: Round. Anther length: About 1 mm. Anther color: 155A. Pollen amount: Scarce. Pollen color: 155A. Pistils: Pistil quantity per flower: Three, fused. Pistil length: About 4 mm. Stigma shape: Oval. Stigma color: 155A. Style length: About 1 mm. Style color: 155A. Ovary color: 155A.

*Fruit.*—Type: Capsule, dehiscent. Length: About 5 mm. Diameter: About 3 mm. Shape: Urn-shaped. Color: Close to 177A.

*Seed.*—Minute, dust-like. Length: Less than 0.5 mm. Diameter: Less than 0.5 mm. Color: Brown.

Disease/pest resistance: Under commercial production conditions, plants of the new *Hydrangea* have not been observed to be resistant to pathogens or pests common to *Hydrangea*.

Weather tolerance: Plants of the new *Hydrangea* have been shown to be tolerant to temperatures ranging from −30 to 33° C. Flowers of plants of the relatively tolerant to wind and rain.

It is claimed:

1. A new and distinct cultivar of *Hydrangea* plant named 'DVP Pinky', as illustrated and described.

* * * * *

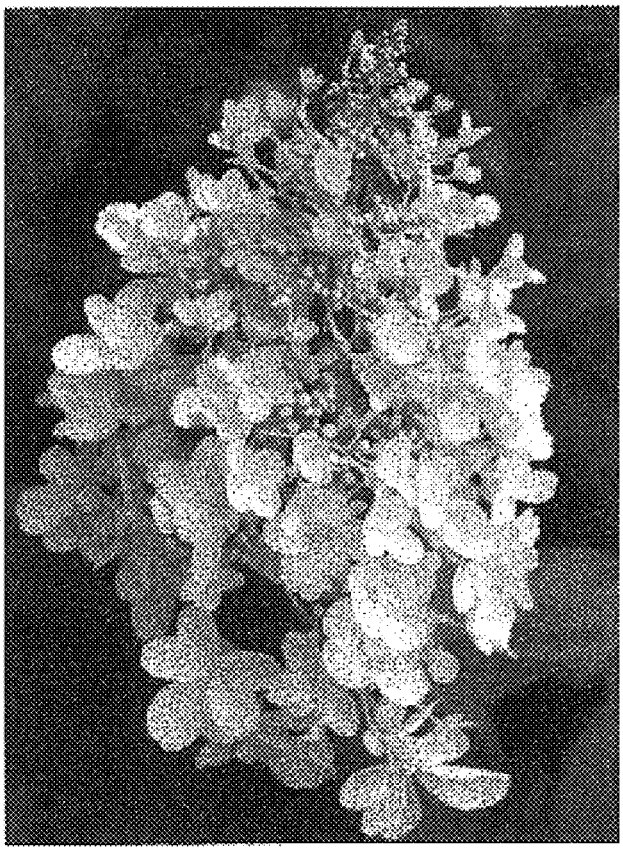
*Inflorescence close up - color in July*
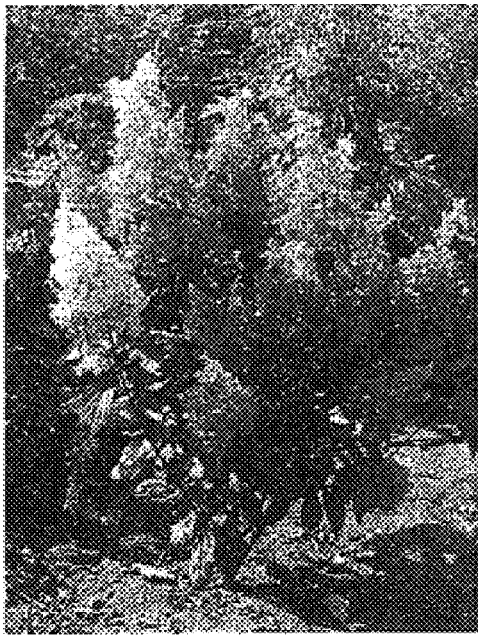
*Inflorescence color in August*